US011642168B2

(12) United States Patent
Varghese et al.

(10) Patent No.: US 11,642,168 B2
(45) Date of Patent: May 9, 2023

(54) LIGHT BASED SKIN TREATMENT DEVICE

(71) Applicant: KONINKLIJKE PHILIPS N.V., Eindhoven (NL)

(72) Inventors: Babu Varghese, Eindhoven (NL); Rieko Verhagen, Vught (NL)

(73) Assignee: Koninklijke Philips N.V., Eindhoven (NL)

(*) Notice: Subject to any disclaimer, the term of this patent is extended or adjusted under 35 U.S.C. 154(b) by 108 days.

(21) Appl. No.: 16/473,647

(22) PCT Filed: Dec. 27, 2017

(86) PCT No.: PCT/EP2017/084648
§ 371 (c)(1),
(2) Date: Jun. 26, 2019

(87) PCT Pub. No.: WO2018/122266
PCT Pub. Date: Jul. 5, 2018

(65) Prior Publication Data
US 2021/0128939 A1 May 6, 2021

(30) Foreign Application Priority Data
Dec. 28, 2016 (EP) .................... 16207164

(51) Int. Cl.
A61B 18/20 (2006.01)
A61B 5/00 (2006.01)
(Continued)

(52) U.S. Cl.
CPC .......... A61B 18/203 (2013.01); A61B 5/0095 (2013.01); A61B 5/4836 (2013.01);
(Continued)

(58) Field of Classification Search
CPC ............... A61N 5/0616; A61N 5/0617; A61N 2005/0632; A61N 2005/067;
(Continued)

(56) References Cited

U.S. PATENT DOCUMENTS 7,282,060 B2    10/2007  DeBenedictis
2009/0248004 A1*  10/2009  Altshuler ............... A61B 18/18
                                              606/33

(Continued)

FOREIGN PATENT DOCUMENTS

CN    105067568 A    11/2015
WO    WO0242719 A2   5/2002
(Continued)

OTHER PUBLICATIONS

PCT International Search Report, International application No. PCT/EP2017/084648, dated Apr. 4, 2018.
(Continued)

Primary Examiner — Mallika D Fairchild
Assistant Examiner — Shreya Anjaria

(57) ABSTRACT

A pulsed laser skin treatment device is for laser induced optical breakdown of hair or skin tissue. The device has a light exit window to be placed against a surface to be treated such as skin during use. A feedback system is used for determining a state of contact between the light exit window and the surface. To this end the feedback system is capable of detecting a feedback signal representative for the state of contact. If the feedback signal or the state of contact is such that the risk of skin surface or device damage by the device operation is too high, the user or the device has a way to interrupt the treatment or to reduce light output to reduce or eliminate this risk.

20 Claims, 4 Drawing Sheets

(51) Int. Cl.
| | |
|---|---|
| *A61N 5/06* | (2006.01) |
| *A61B 18/00* | (2006.01) |
| *A61B 90/00* | (2016.01) |
| *A61B 17/00* | (2006.01) |
| *A61N 5/067* | (2006.01) |

(52) U.S. Cl.
CPC .......... *A61N 5/0616* (2013.01); *A61B 5/0059* (2013.01); *A61B 2017/00057* (2013.01); *A61B 2017/00154* (2013.01); *A61B 2018/0047* (2013.01); *A61B 2018/00642* (2013.01); *A61B 2018/00779* (2013.01); *A61B 2090/065* (2016.02); *A61N 5/067* (2021.08); *A61N 5/0617* (2013.01); *A61N 2005/0626* (2013.01); *A61N 2005/0632* (2013.01)

(58) Field of Classification Search
CPC .. A61N 2005/0626; A61B 2017/00057; A61B 2017/00154; A61B 2018/00779; A61B 2018/00642; A61B 2090/065
See application file for complete search history.

(56) References Cited

U.S. PATENT DOCUMENTS

| | | |
|---|---|---|
| 2012/0059307 A1 | 3/2012 | Harris et al. |
| 2012/0123444 A1 | 5/2012 | Verhagen |
| 2012/0283710 A1* | 11/2012 | Liu ........................ A61B 18/20 606/9 |
| 2012/0283711 A1 | 11/2012 | Harvey |
| 2015/0038953 A1 | 11/2015 | Verhese |
| 2016/0178680 A1* | 6/2016 | Ntziachristos ....... G01N 29/265 73/643 |
| 2016/0270848 A1 | 9/2016 | Varghese et al. |

FOREIGN PATENT DOCUMENTS

| | | | |
|---|---|---|---|
| WO | WO2005011510 A1 | 2/2005 | |
| WO | WO2008001284 A2 | 1/2008 | |
| WO | WO2008089344 A2 | 7/2008 | |
| WO | WO2014113574 A1 | 7/2014 | |
| WO | WO-2014174010 A1 * | 10/2014 | ............. A61B 18/20 |
| WO | WO-2015177750 A1 * | 11/2015 | ........... A61B 18/245 |
| WO | WO2015177750 A1 | 11/2015 | |

OTHER PUBLICATIONS

Habbema L. et al., "Efficacy of minimally Invasive Nonthermal Laser-Induced Optical Breakdown Technology for Skin Rejuvenation", Lasers in Medical Science 28 (3), 935-940 (2013).

Habbema L. et al., "Minimally Invasive Non-Thermal Laser Technology Using Laser-Induced Optical Breakdown for Skin Rejuvenation," Journal of Biophotonics 5 (2), 194-199 (2012).

* cited by examiner

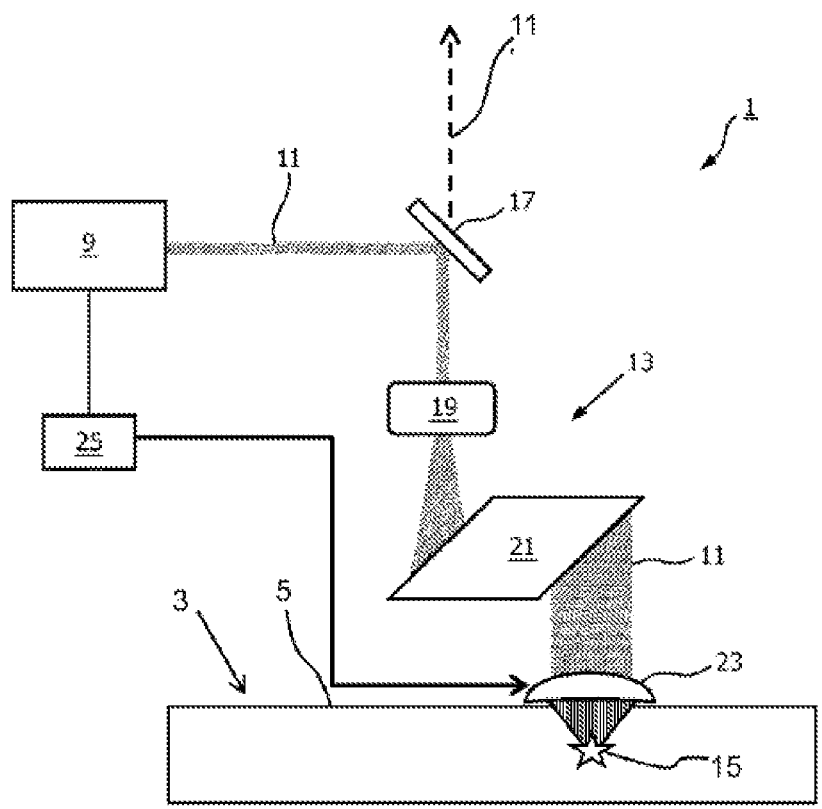
FIG. 1A  [Prior Art]
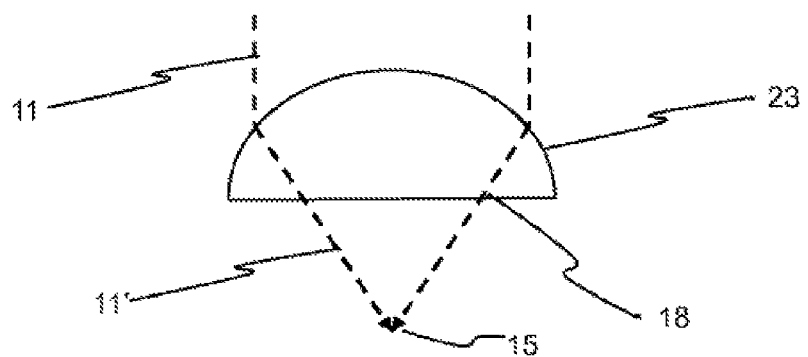
FIG. 1B  [Prior Art]

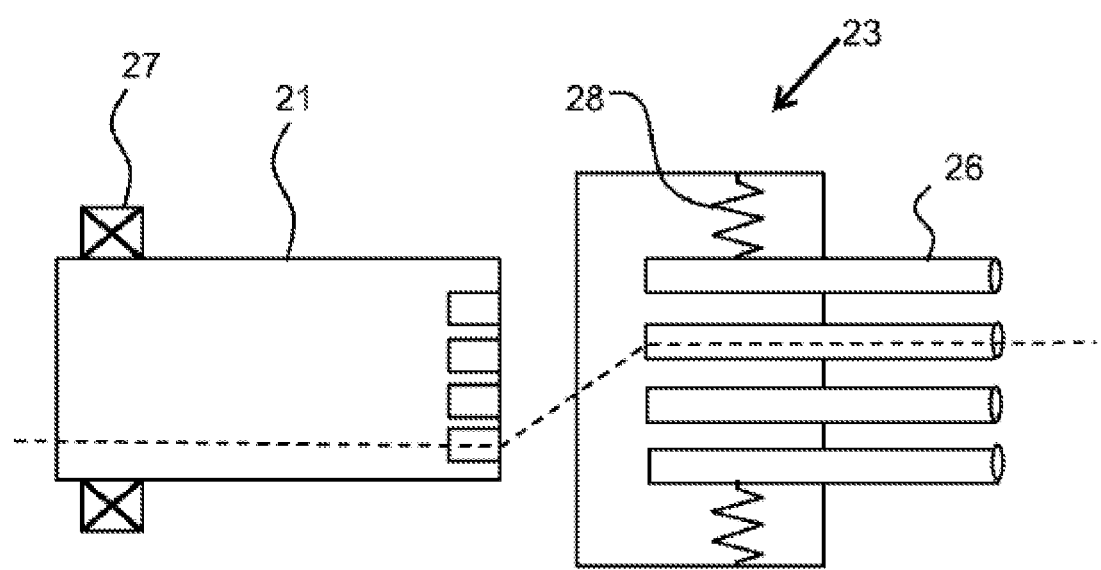
FIG. 2 [Prior Art]

LIGHT BASED SKIN TREATMENT DEVICE

CROSS-REFERENCE TO PRIOR APPLICATIONS

This application is the U.S. National Phase application under 35 U.S.C. § 371 of International Application No. PCT/EP2017/084648, filed on Dec. 27, 2017, which claims the benefit of EP Patent Application No. EP 16207164.1, filed on Dec. 28, 2016. These applications are hereby incorporated by reference herein.

FIELD OF THE INVENTION

The invention pertains to a device and method for treatment of tissue of a subject by laser induced optical breakdown (LIOB). The device and method make use of focusing of a light beam through a light exit window which is for contacting the tissue when the device is in use.

BACKGROUND OF THE INVENTION

Such devices are sometimes referred to as light based skin treatment devices and can be used for e.g., skin rejuvenation, wrinkle treatment and hair cutting. In light based wrinkle treatment, the device creates a focal spot in a dermis layer of the skin to be treated. The power and pulse duration of the laser and the dimension of the focal spot are selected such that a laser induced optical breakdown (LIOB) phenomenon affects the skin in order to stimulate re-growth of skin tissue and, therewith, to reduce wrinkles. In light based hair cutting, the incident light beam is focused inside the hair and the LIOB phenomenon causes the hair to be cut through.

For example, the international patent application published as WO 2005/011510 describes a device for shortening hairs comprising a laser source for generating a laser beam during a predetermined pulse time, an optical system for focusing the laser beam into a focal spot and a laser beam manipulator for positioning the focal spot in a target position. A dimension of the focal spot and a power of the generated laser beam are such that in the focal spot the laser beam has a power density which is above a characteristic threshold value for hair tissue above which, for the predetermine pulse time, a laser induced optical breakdown (LIOB) phenomenon occurs in the hair tissue.

In general, laser induced optical breakdown (LIOB) occurs in media, which are transparent or semi-transparent for the wavelength of the laser beam, when the power density (W/cm$^2$) of the laser beam in the focal spot exceeds a threshold value which is characteristic for the particular medium. Below the threshold value, the particular medium has relatively low linear absorption properties for the particular wavelength of the laser beam. Above the threshold value, the medium has strongly non-linear absorption properties for the particular wavelength of the laser beam, which are the result of ionization of the medium and the formation of plasma. This LIOB phenomenon results in a number of mechanical effects, such as cavitation and the generation of shock waves, which damage the medium in positions surrounding the position of the LIOB phenomenon.

It has been found that the LIOB phenomenon can be used to break and shorten hairs growing from skin. Hair tissue is transparent or semi-transparent for wavelengths between approximately 500 nm and 2000 nm. For each value of the wavelength within this range, LIOB phenomena occur in the hair tissue at the location of the focal spot when the power density (W/cm$^2$) of the laser beam in the focal spot exceeds a threshold value which is characteristic for the hair tissue. Said threshold value is rather close to the threshold value which is characteristic for aqueous media and tissue and is dependent on the pulse time of the laser beam. In particular, the threshold value of the required power density decreases when the pulse time increases.

In order to achieve mechanical effects as a result of the LIOB phenomenon which are sufficiently effective so as to cause significant damage, i.e. at least initial breakage of a hair, a pulse time in the order of, for example, 10 ns suffices. For this value of the pulse time, the threshold value of the power density of the laser beam in the focal spot is in the order of $2*10^{10}$ W/cm$^2$. For the described pulse time and with a sufficiently small dimension of the focal spot obtained, for example, by means of a lens having a sufficiently large numerical aperture, this threshold value can be achieved with a total pulse energy of only a few tenths of a millijoule.

The effectiveness of optical breakdown for skin rejuvenation depends on several factors such as optical and structural properties of the skin, laser intensity in the focus, optical coupling etc. In many cases, the treatment depth can be different, depending on the thickness of stratum corneum and epidermis.

SUMMARY OF THE INVENTION

A problem which can arise is that the exit window can be damaged by the products of the LIOB, such as e.g. shock wave, plasma, high power density. Especially since the device is configured such that the LIOB generally occurs close to the light exit window. A damaged exit window has a detrimental effect on the ability of the device to provide a sufficiently tight focus at the desired position, which may reduce the efficacy of the treatment process. In addition or alternatively, such damage may increase the occurrence of adverse side effects of the treatment, such as skin irritation. In particular, if superficial lesions are created above dermis by focus depth change due to damage, petechiae (microbleeding) may occur due to the micro-rupturing of capillaries, resulting again in reduced efficacy and increased side effects leading to much unwanted social down time needed for recovery of a person treated. There is therefore a need for a device and method which are able to address the aforementioned problem, i.e. to reduce or prevent exit window damage and/or such skin irritation during use of the device or method.

The invention is defined by the claims.

In accordance with a first aspect there is provided a device for treatment of tissue of a subject by laser induced optical breakdown, the device comprising:

a light source for providing a pulsed light beam;

a focusing system for receiving the pulsed light beam and outputting a focused pulsed light beam with a focal spot that can be positioned in the tissue;

a light exit window having a contact surface for contacting the tissue during use of the device and for allowing the pulsed light beam to exit the device through the contact surface before it reaches the focal spot;

wherein the device comprises a feedback system for detecting a feedback signal dependent of a state of contact between the contact surface and the tissue.

The tissue preferably is tissue of a mammal such as hair, skin or organ surface or boundary tissue of [[ ]] e.g. an animal or human being. Tissue typically is tissue of a human or animal subject. The tissue may be skin.

The light source and the focusing system are suitable for causing laser induced optical breakdown of the tissue in the focal spot when the focal spot is positioned in the tissue. This means that together they provide a focal spot in which a high enough power density of light is present for causing the laser induced optical breakdown.

The light source can be a laser. The light exit window is at least partly transparent for the laser light.

The exit window can take any shape as long as it allows exiting of the pulse light form the device in order to have it enter the tissue. The light exit window can be separate from the focusing system, but can also be part of it. The contact surface of the light exit surface can be such that it does not change the convergence of a passing light beam. Alternatively, it may also be designed to change beam convergence (e.g. a convex surface for increasing beam convergence for e.g. aiding the focusing). The exit window can be of a lens surface or other optical surface.

The light exit surface has a contact surface intended to be in contact with a surface of the tissue when the device is in use. The contact can be achieved in a direct way with the contact surface against the surface of the tissue with or without an index matching fluid in between, but can also involve one or more transparent sheets positioned in between these surfaces, again with one or more index matching fluids between the multiple surfaces in contact.

The state of contact during normal use of the device should be such that this use does not substantially cause damage to the device, exit window or tissue surface.

Contact can mean optical contact and/or contact with which a reflectivity and/or scattering of the beam when exiting the device and/or entering the tissue is so large as to cause the unwanted damages.

The device and method make use of a feedback system and method that can detect a feedback signal that is dependent on the state of contact. Hence the state of contact can be determined (measured) and if it is found to be insufficient in view of the above, then the power density of the light pulses can be reduced. Conversely, the power density can also be increased if a contact is determined to be sufficient (again). The feedback can thus be used to provide improved contact with the tissue and uniform optical coupling, as well as preventing contact window/exit lens damage and tissue damage. This gives improved safety and efficacy of the treatment.

The feedback signal can be also used to determine whether or not the focal spot is in the tissue. This feedback system is able to ensure that sufficient lesions are created by optical breakdown to have its effect (such as e.g. skin rejuvenation) by ensuring that they are created only in the tissue. This enhances the efficacy of the treatment with minimal side-effects and, in case of skin tissue, possible social down time.

The feedback system may be further adapted to determine a state of contact based on, or from the detected feedback signal.

The device wherein the control unit comprises a user interface for providing to a user a user-perceivable representation of the feedback signal and/or an indication of the determined state of contact. Hence a user can decide to reduce the power density if he notices insufficient contact from the user interface.

The feedback system is preferably for changing the power density of the focused pulsed light beam in dependence of the feedback signal and/or the determined state of contact. Hence upon feedback further damage may be prevented or reduced due to reduced power density. Conversely, if a desired contact has been established power density can be increased to use level for creation of LIOB.

Changing of the power density can comprise:
comparing the feedback signal with a threshold signal, or the determined state of contact with a desired state of contact, the threshold signal being associated with the desired state of contact and the desired state of contact being a state of contact good enough for preventing substantial damage to the device or to the surface of the tissue,
reducing the power density, if the comparison of the feedback signal with the threshold signal is indicative for a state of contact less good than that of the desired state of contact. In addition or alternatively, it can comprise increasing the power density, if the comparison of the feedback signal with the threshold signal is indicative for a state of contact that is as good as the desired state of contact or better.

Reducing the power density can comprise reducing the power density to zero or a value below the threshold value for LIOB generation in the relevant medium which may be preferably air, but can also be tissue, or another medium used for creating the contact at the contact surface.

Changing of the power density can comprise changing the power of the focused pulsed light beam and/or the focusing or beam shape of the focused pulsed light beam. The power density needed for the LIOB holds for the focused beam and in particular the focal spot. Its change can involve feedback signal dependent control of different devices either alone or in combination. A controller for reducing or increasing the power output of the light source can be used. A beam attenuator for attenuating the light beam that reaches the focal spot can be used. For example there may be an aperture, filter, or beam deflector that can be placed in the beam. A device for reducing or increasing the quality of the focus in the focal spot can be used. For example the focusing system can be controlled to increase the distance between focal spot and contact surface of the light exit window. Also a light scattering device can be used which when in the beam or when having increased scattering modus reduces the quality of the focus.

There may be a controller for reducing or deactivating the light source or preventing the incident light from reaching the skin when the quality of the contact drops below a threshold contact, i.e. when the pressure or force drops below a threshold. The controller may operate e.g. a shutter or light beam deflection device for the latter purpose.

The feedback signal may comprise sound generated by the focused pulsed light beam, the feedback system comprises a device for detecting the sound and the feedback system is further for determining the state of contact from one or more characteristics of the sound. A microphone can be used as the detector, but preferably the detector is a hydrophone for measuring an acoustic signal. The high energy deposited on the tissue in the focus creates thermal (thermoelastic expansion), optical (plasma spark), and acoustic phenomena. The acoustic signal comprises or consists of a characteristic broadband audible acoustic wave, resulting from the supersonic expansion of the generated shock waves, and the expansion of the plasma wave associated to it. The acoustic emission from laser-produced plasmas may for example be detected using a dynamic microphone placed at an approximate distance of a few ems from the plasma. The preferred characteristic acoustic frequency is in the range of the 3 to 16 kHz. This works well for skin tissue.

The feedback system thus preferably is for identifying spectral characteristics in the sound. For example frequencies or peaks in the hydrophone output which provide an indication of the material in which LIOB has taken place. If not in tissue, then contact is not in order.

Instead of or in addition to the sound signal, the feedback signal can comprise light dependent on the state of contact, the feedback system comprises a device for detecting the light and the feedback system is further for determining the state of contact from one or more characteristics of the light. The device is an optical device, and the contact can be evaluated from light reflected by the contact surface or tissue surface. The device can have a second light source for providing second light to the contact surface to be reflected at least partly by the contact surface and for which the reflectance is dependent on the state of the contact. The device then also has a detector for detecting such reflected light. TIR can be used. The wavelength and or intensity may be or preferably are different (intensity lower than) from that of the pulsed light beam. Also, a LIOB event whether or not occurring in tissue may generate light that in general may be indicative of a state of contact. LIOB in air or other medium than tissue being indicative of an insufficient contact.

Preferably the light is generated by the pulsed light beam or the focused pulsed light beam. Also this light will be reflected to some extent by contact surfaces for which index matching is not perfect. Hence the quality of contact will also cause a change of reflected pulsed light. This embodiment makes the need for a second light source and detector not needed. The device can thus be simpler and more robust.

The light for feedback is preferably originating from the contact surface. In this way the most reliable feedback is provided as the light does not depend on whether or not LIOB has taken place or not.

The device for detecting the light can comprise an image sensor and the feedback system is further for determining the state of contact from one or more characteristics of an image captured by the image sensor.

The device may comprise an image sensor and an image processor. The focal point can be detected based on a characteristic optical flash (plasma spark) associated with LIOB. Typically the broad spectral range of the characteristic flash is in the wavelength range of 400-1100 nm. The emission spectra from the plasma can be measured using a combination of a spectrometer and an intensified charged coupled device detector (ICCD). Depending on the focal position, the flash spectra exhibits spectral peaks that are characteristic of the material in the focus (glass interface, immersion medium, tissue such as e.g. skin etc.) and can be used as a signature of the focal point and also as an indicator whether LIOB has taken place.

The image processor is thus preferably for identifying spectral peaks in the light received from the tissue which provide an indication of the material in which LIOB has taken place.

The image processor may additionally be adapted to analyze an image captured by the image sensor to determine a quality of contact between the focusing system and the tissue.

In this way, optical analysis can also be used to determine both the depth of focus and the quality of optical contact of the system with the tissue.

The quality of the contact can be measured based on the uniformity of specular reflection in the images captured by simple monochrome or RGB cameras. In the case of optimal and uniform coupling, the intensity distribution follows a homogenous Gaussian distribution. Image features and non-uniformities are representative of reduced optical contact quality.

Thus, the image processor may be for identifying non-uniformities in the image captured which are representative of the quality of contact.

The image processor may be adapted to analyze an image captured by the image sensor to determine a level of tissue color change such as e.g. skin redness. In this way, the treatment can be halted if a level of irritation beyond an acceptable threshold is detected. Thus, the feedback system may implement both preventative measures to prevent excessive irritation but also have a safety net which detects when the treatment has resulted in an unacceptable level of irritation.

The feedback system for detecting light received from the skin comprising an image sensor and an image processor, wherein the image processor is adapted to analyze an image captured by the image sensor to determine a level of coloration of the tissue. Preferably the level of coloration is a level of skin redness. This relates to e.g. the aspect of analyzing skin redness, as explained above.

In this case, a controller may be provided for deactivating the light source or preventing the incident light from reaching the skin when a level of skin redness exceeds a threshold. Again, the controller may operate e.g. a shutter or light beam deflection device for implementing the prevention.

In addition to the aforementioned or alternative to the aforementioned feedback signal, the feedback signal can comprise a force or pressure dependent on the force or pressure with which the light exit window is pressed against the tissue during use of the device, the feedback system comprises a detector for detecting the force or pressure and the feedback system is for determining the state of contact based on, or from the force or pressure. If contact force or pressure is insufficient, optical contact may also be insufficient. For example no contact pressure may indicate insufficient contact.

Preferably there is also provided an output system for giving an indication to the user of the applied pressure or force. Comparison of the monitored pressure or force with a reference pressure or force may be performed in order to indicate whether or not the applied pressure or force is a suitable pressure or force. The pulse provision may be interrupted automatically when the applied pressure or force is below the reference value.

In this way, the user is guided to apply a pressure or force which is suitable to maintain a required contact with the tissue.

In all examples, a controller may be provided for reducing the power density such as by deactivating the light source when it is determined that the treatment should stop, because the focal point is determined not to be in the tissue, or there is excessive tissue color change (e.g. skin redness), or there is poor contact detected. This provides a safety cut-off.

Any of the embodiments described herein before can also include a controller for controlling the light source and/or the focusing system and/or the feedback system. Such a controller can be in the form of an electrical circuit such as an IC or computer.

Another aspect of the invention provides a method of treatment of tissue of a subject by laser induced optical breakdown, the method comprising:

providing a pulsed light beam;

focusing the pulsed light beam into a focused pulsed light beam with a focal spot positioned in the tissue;

providing a light exit window having a contact surface in contact with the tissue and allowing the pulsed light beam to exit the device through the contact surface before it reaches the focal spot, the light exit window having a contact surface for contacting the tissue during use of the device;

detecting a feedback signal dependent of a state of contact between the contact surface and the tissue.

It will be clear that features described for the device herein above may be converted to corresponding features for the method and they will have the same advantages and solve the same problems.

The method can further comprise determining a state of contact based on, or from the detected feedback signal.

The method can comprise changing the power density of the focused pulsed light beam in dependence of the feedback signal and/or the determined state of contact.

The measures outlined above may also be employed, such as analyzing an image captured by the image sensor to determine a quality of contact between the focusing system and the tissue and then deactivating the light source when the quality of contact is determined to be below a threshold level.

The feedback system may also be used for detecting a sound generated by a light source pulse, thereby to determine whether or not the focal spot is in the tissue. In this case, the light source is deactivated when the focal spot is determined not to be in the tissue.

The feedback system discussed above for monitoring a pressure applied to the device against the tissue may also be employed, in which an output system is used for providing an indication to the user as to whether or not a suitable pressure is being applied. In this case, the light source is deactivated when the pressure is determined not to be suitable.

The invention also provides a light based skin treatment method comprising:

providing a pulsed light beam for treating tissue by laser induced optical breakdown of the tissue;

focusing the incident light beam into a focal spot in the tissue; and detecting light received from the tissue and detecting a sound generated by a light source pulse, thereby to determine whether or not the focal spot is in the tissue.

The invention also provides a light based tissue treatment method comprising:

providing a pulsed light beam for treating tissue by laser induced optical breakdown of the tissue;

focusing the incident light beam into a focal spot in the tissue; and sensing a pressure applied to the device against the tissue, and providing an indication to the user as to whether or not a suitable pressure is being applied.

The invention also provides a light based tissue treatment method comprising:

providing a pulsed light beam for treating tissue by laser induced optical breakdown of the tissue;

focusing the incident light beam into a focal spot in the tissue; and detecting an image of light received from the tissue and analyzing the image to determine a level of tissue coloration such as [[ ]] e.g. skin redness.

These methods are non-therapeutic methods, in particular cosmetic methods, for e.g. skin rejuvenation, wrinkle reduction, or hair removal.

BRIEF DESCRIPTION OF THE DRAWINGS

Examples of the invention will now be described in detail with reference to the accompanying drawings, in which:

FIGS. 1A and 1B schematically show a known LIOB skin treatment device;

FIG. 2 shows a known way to implement focal depth control;

DETAILED DESCRIPTION OF THE EMBODIMENTS

Figure 3:
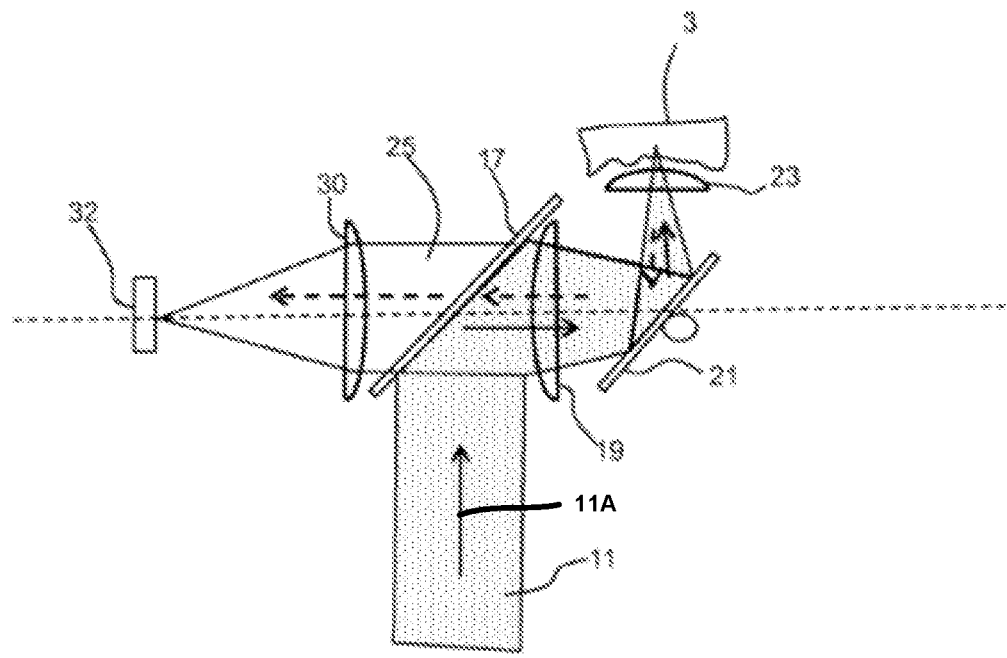
FIG. 3 shows a device with a first example of feedback system.

Disclosed is a pulsed laser skin treatment device for laser induced optical breakdown of tissue of mammals such as in particular skin tissue. The disclosure also relates to feedback systems for controlling the system to prevent damage to the exit window of the focusing system 23 and/or to stop or prevent skin irritation.

First an example will be given of the type of device for which the feedback system can be used.

FIGS. 1A and 1B show a device 1 for treatment of a tissue 3 having a surface 5. In this case the tissue is exemplified by a skin 3, but other tissues can be treated.

The system 1 comprises a light source 9 for generating a laser beam 11 during at least a predetermined pulse time, and it comprises an optical system 13 for manipulating the laser beam 11 and focusing the beam into a focused beam[[ ]] and into a focal spot 15 and for positioning the focal spot 15 in a target position within the skin 3. The skin is at least partly transparent to the light from the light source 9. The device includes a light exit window 18 through which the pulsed light beam exits the device. In this case the light exit window is flat and does not change the beam convergence of the focused beam 15. This may be different when the light exit window is convex for example. Also in this case the light exit window is part of the focusing system 23. The feedback system can be used for all.

The light source 9 is configured to emit a predetermined number of laser pulses at a predetermined wavelength and with a predetermined pulse duration and repetition rate. The system 1 is configurable such that the target position of the focal spot 15 is beneath the surface of the skin. The dimension of the focal spot 15 and the power of the generated laser beam are such that, in the focal spot 15, the laser beam 11 has a power density, which is above the characteristic threshold value for the skin tissue, above which, for the predetermined pulse time, a laser-induced optical breakdown event can occur or occurs.

A suitable light source comprises a Q-switched Nd:YAG laser emitting laser pulses at a wavelength of about 1064 nm with a pulse duration of about 5-10 ns, although other lasers, e.g. a Nd:Cr:Yag 3-level laser and/or diode lasers may be used as well. A 1064 nm laser is preferably used for treatment because of the relative low absorption and scattering inside the skin and thereby providing large penetration depth. Other wavelengths may be used particularly in the near infrared range.

The light source 9 is controllable with an optional controller 25, which may provide a user interface.

The example of the optical system 13 schematically indicated in FIG. 1 comprises a beam deflection and dichroic beam splitting system 17, an aberration correcting system 19, a beam scanning system 21 and a focusing system 23, which systems may comprise one or more mirrors, prisms, beam splitters, polarizers, optical fibers, lenses, apertures, shutters, etc. For example, the scanning system comprises scanning prisms.

The optical system 13, in this case has focusing depth selection (but this is not needed per se), beam shaping and focusing and a contact/output window which is for contacting the skin surface. In this case there is also a contour following suspension (not shown in FIG. 1) to maintain contact of the contact/output window with the skin surface during use of the device.

One or more parts of the optical system 13 may be controllable with an optional controller (not shown), which may be integrated with the light source controller 25 to control one or more properties of the target position and/or the focal spot.

Laser beam focusing parameters may be determined by appropriate settings of a beam shaping and/or the focusing system, e.g. by adjustment of the numerical aperture of the focusing system. Suitable values for the numerical aperture NA of the focusing system may be chosen from a range 0.05<NA<nm, wherein nm is the index of refraction of the medium for the laser wavelength, during operation.

There may be an articulating arm between the laser source 9 and the beam deflection and dichroic beam splitting system 17. The beam deflection system 17 and subsequent components form part of a hand piece. Because of alignment errors in the mirrors of the articulating arm, the beam may be expanded before entering the articulating arm and then compressed afterwards before beam steering and aberration correction. However, other propagation means of laser beam guidance may be used.

At least part of the optical system 13 and/or the beam path of the laser beam 11 may be enclosed, e.g. for eye-safety, e.g. comprising opaque tubes and/or one or more optical fibers.

The focusing depth provided by the focusing system 23 is preferably adjustable. FIG. 2 shows a known way to implement such adjustment. The focusing system 23 comprises a set of output windows 26 each with a different focus depth, and an optical path is provided to one of the output windows by the scanner motor 27, which rotates the scanning system 21. The output windows 26 are held by a contour following suspension 28. The output windows are thus arranged around a circular path, and a notch system provides positioning with respect to the scanning system 21. There may be four output windows, and thus four lens sets each separately spring loaded to provide contour following.

The scanning system 21 is used to scan the focus across an area of skin.

One example of laser that may be used in the system of FIG. 1 has a maximum repetition frequency of 1000 Hz, and a typical treatment regime uses a lesion pitch of 200 μm, resulting in a typical maximum scan speed of 200 mm/s. This scan speed rules out any manual-scanning-only options because of lack of control when applying these scanning speeds by hand.

Additionally, any start-stop scanning system will be severely challenged to reach this scanning speed over a short distance of acceleration, leading to mechanical vibrations and ineffective use of the capacity of the laser. A more easily controlled slower scanning speed will significantly increase the treatment time for large surface areas.

To overcome this challenge a continuous motion scanning may be used on the basis of rotary motion, which can easily achieve these scan speeds and does not suffer from strong vibrations and ineffective use of the laser capabilities.

For this purpose a rotating prism may be used.

A first possible prism design comprises a rhomboid. Two opposite parallel end faces function as total internal reflection faces. They are at 45 degrees to the incident light direction. The two internal reflections in the prism provide a lateral shift of an incident beam, so that exit beam is parallel but laterally shifted relative to the input beam. By rotating the prims about an axis perpendicular to the lateral shift direction, and therefore parallel to the incident beam direction a circular path is swept by the output beam. The rotation is about the axis of the input beam. The radius of the circle swept is the length of the rhomboid. Rhomboid prisms can be manufactured with anti-reflection coatings on the faces where required.

A second possible prism design is a dove prism. The two end faces function as refraction interfaces, and the bottom face functions as a total internal reflection face. The end faces are at 45 degrees to the incident light. The two refractions and the single total internal reflection in the prism again provide a lateral shift of an incident beam, so that exit beam is parallel but laterally shifted relative to the input beam. By rotating the prims about an axis perpendicular to the lateral shift direction, and therefore parallel to the incident beam direction, a circular path is swept by the output beam. The rotation is about the axis of the input beam. The amount of beam translation depends on the position of the incident beam relative to the input surface of the dove prism and on the size of the prism. The prism is rotated around the chief incident ray. Anti-reflection coatings may again be added on the angled surfaces to reduce losses by reflection.

The rotating prism is mechanically balanced to avoid vibration. A prism mount is suspended on ball bearings and connects directly to a motor rotor so as to minimize the influence of the aberration correction settings on the effective numerical aperture of the focused light.

The skin 3 comprises multiple layers with different optical properties. The epidermis is composed of the outermost layers and forms a waterproof protective barrier. Underneath the epidermis, the dermis is situated. The dermis comprises the collagen fibers at which the skin treatment is aimed. The purpose of the skin treatment and the device such as that of FIGS. 1 and 2 is to create the focus 15 of the pulsed laser beam 11 in the collagen of the dermis in order to create microscopic lesions which result in new collagen formation. It is a further aim to leave the epidermis intact as much as possible.

However, the outermost layer of the epidermis, i.e. the stratum corneum, due to its microscopic fluctuations in roughness, impedes the coupling of light between the device 1 and the skin 3. This coupling is important as the creation of LIOB requires high power density within the skin such that the laser beam power densities at the focusing elements, output window and skin surface are high enough to cause damage to these systems and or the skin when optical coupling is insufficient.

To improve the optical contact of the output window with the skin, a coupling fluid is preferably provided between the focusing system and the tissue, with a refractive index which aims to match that of the tissue and/or an exit lens/window of the focusing system. Nevertheless, even with such coupling fluid present, during use of the device by a user the focusing system may have to be moved over a skin area, which is prone to errors that may cause deterioration of the optical contact. It is therefore important to have feedback on the quality of contact during use of the device to be able to keep such contact, or restore such contact to above a desired level for reducing or preventing the damage indicated above.

A first example of a device having a feedback system which combines optical and acoustic analysis, in order to detect the focus depth at which LIOB is occurring. The feedback system then enables the laser to be switched off if the focus is not in the skin.

This is based on the differences in the wavelength spectrum of a visible flash (plasma spark) and acoustic frequencies of the signal generated during LIOB, which show significant differences depending on the medium in which it occurs, such as air, the lens, the coupling medium and the skin.

The emission spectra can be measured using a combination of a spectrometer and an intensified charged coupled device detector (ICCD). Depending on the focal position, the flash spectra exhibits spectral peaks that are characteristic of the material in the focus (glass interface, immersion medium, skin etc.) and can be used as a signature of the focal point and also as an indicator whether LIOB has taken place.

For instance, in the absence of LIOB, the detector records a flat background spectrum without any spectral features. As an example, the characteristic peaks occurring around 212.4 nm (Si) and 589 nm (Na) can be used for confirming that LIOB is occurring in the glass interface and skin respectively. Other spectral peaks can also be used as indicator of the material. For irradiance threshold below the optical breakdown, flashes without LIOB can also be measured and the differences in the spectral characteristics of the optical flash with and without optical breakdown can also be used a signature.

FIG. 3 shows a first example, based on a confocal system for detecting focus depth.

The same components are given the same reference numbers as in FIG. 1. The aberration correction system 19 comprises an aspheric lens and the focusing system 23 comprises a lens which functions as microscope objective. The visible light optical feedback signal 25 transmitted through the dichroic beam splitter 17 is focused by a plane convex lens 30 onto an image sensor 32 for example a CCD chip.

This arrangement provides confocal detection of the focusing depth to prevent LIOB outside the skin and to determine the focusing depth inside the skin.

The optical paths of the confocal microscope formed by lenses 30 and 23 (illumination and detection) and the LIOB treatment beam are coupled together by the dichroic beam splitter 17. The confocal microscope makes depth resolved images of the focal position and thus enables a verification of the treatment depth. This verification is carried out using image processing of the image captured by the image sensor, and the verification is used by the controller 25 to activate or deactivate the laser 9.

Figure 4:
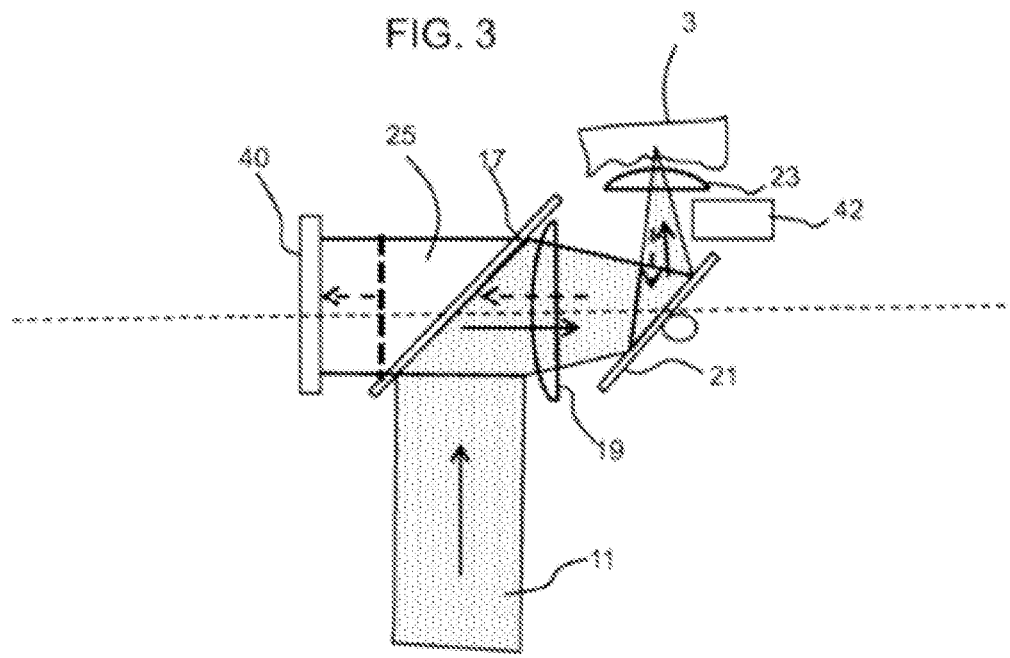
FIG. 4 shows a device with a second example of feedback system.

FIG. 4 shows a second example, based on providing a feedback system based on both light and sound.

The same components are given the same reference numbers as in FIG. 3. An image sensor is no longer needed, and instead there is a photodiode or photodiode array 40 and optionally an associated diffraction grating for analyzing a spectrum of the visible light 25, rather than an image formed. A needle hydrophone 42 enables analysis of a spectrum of a sound wave.

The visible light flash and acoustic signal generated during LIOB exhibits different spectral and acoustic characteristics in air, in the coupling medium and in the skin. During the occurrence of the LIOB, the visible flash can be recorded by the photodiode 40 (or by a grating) and the acoustic signal is recoded by means of the hydrophone. The combined detection of the flash and the acoustic signal enables the focusing depth to be determined.

The visible light received from the skin is the result of a photomechanical mode of interaction which occurs in Laser induced optical breakdown. It involves the massive generation of free electrons. The process is termed 'electron avalanche growth' or the 'inverse Bremsstrahlung effect'. The formation of plasma results in a white light continuum that has little intensity variation as a function of wavelength. This light is caused by Bremsstrahlung and recombination radiation from the plasma as free electrons and ions recombine in the cooling plasma.

Instead or as well as determining a focal depth, the system of FIG. 3 may be used to analyze the quality of the optical coupling between the skin and the output lens of the focusing system 23. If the optical coupling is not effective, optical breakdown can occur in the air or in the exit surface of the lens, leading to lens and skin damage.

In order to implement optical feedback the beam deflection and dichroic beam splitting system 17 comprises a dichroic beam splitter which reflects the laser light but passes visible wavelength light. Thus, received visible wavelength light from the skin 3 is captured by the optical system and is provided as a feedback signal 11A which can be used for controlling the system either manually or automatically.

In this first example light generated by a LIOB event is used as feedback.

However, a separate source of light can be used. To this end a light beam of this source is coupled to the light path such that it reaches the contact surface. A reflectance of this light is then collected at the detector 32.

The analysis of the optical coupling may be achieved based on image processing of the image captured by the image sensor 32.

The quality of the contact can be measured based on the uniformity of specular reflection in the images captured by simple monochrome or RGB cameras. In the case of optimal and uniform coupling, the intensity distribution follows a homogenous Gaussian distribution. Larger amounts of image features such as the size of intensity spots, number of spots, the size of the largest spot etc. can be derived from these images after thresholding and these features can be used as indictors of non-optimal coupling.

The system of FIG. 3 may also be modified by removing the image sensor 32 and lens 30 and instead providing an output window to enable visual inspection by a user of the system. The user can then visually inspect the skin contact appearance at each laser flash. Again, this will be visible as imperfections such as image spots.

A further option for detecting the skin contact quality is to use a spring-loaded focusing lens system to provide contour following, with feedback of a measured load. The complete optical system is spring loaded so that the optical paths between optical components are preserved.

Figure 5:
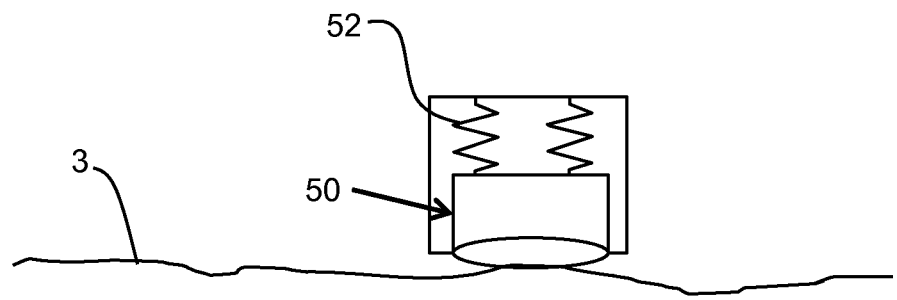
FIG. 5 shows a device with a third example of feedback system.

FIG. 5 shows an optical system 50 including at least the final objective lens which is spring loaded by springs 52 to enable the device to follow the contour of the skin 3. This allows seamless tracking of the curved skin surface while scanning.

Feedback based on the load in the system is used to control the laser activation. A set of reference load values may be used to ensure optimal contact and thereby act as a reference for the spring system.

Feedback is then provided to enable the user to maintain the load within the desired range of load levels. This range of load levels is preferably between (and therefore excludes)

full spring extension (zero load) and maximum spring compression (maximum load) since both of these are inappropriate to maintain good contact.

At least two contact points are defined in close proximity to ensure proper contour following of both small local skin features as well as larger global skin contours and features.

In all feedback options of the current disclosure and examples, the output to the user may be provided on a screen of the system, or it may be sent as a wireless signal to a smart phone, watch, or other nearby device with wireless connectivity. The instructions to the user may be audible, for example with a warning sound when the pressure being applied is too low or too high, and/or a visual output may be provided. Such output may be provided up to a point where feedback indicates such poor quality of contact that the risk of damage to device or treated subject is too high. A threshold level may be set by a user or may be predetermined by the device. Upon reach of such threshold the device can then prevent the laser beam from reaching the optical system, and/or output window and or skin surface. This may encompass shutoff of the laser source or prevention of the beam reaching these parts. Shutters may be used for this which are operated by a controller based on the feedback signal.

If superficial lesions are created at the upper part of, or above the dermis such as in the epidermis, skin redness (erythema) may occur. Furthermore, if such lesions are created in the upper part of or just above the dermis petechiae (micro-bleeding) may occur. Both such effects may arise as a result of poor optical contact between the focusing system (or exit window) and the skin, or resulting from damage to the focusing system.

The feedback approaches above aim to reduce or prevent such damage or prevent laser operation when there is poor optical contact. However, to this end an alternative (or additional) approach is to detect the presence and/or extent of erythema (skin redness) and/or the presence and/or extent of petechiae (micro-bleeding) occurring at the skin, and thereby provide an indication of quality of contact to the user. Early signs of skin damage may be used as the feedback to react on with a sign to the user or even automatic stop of treatment by halting the device.

The feedback system is then based on measuring the presence and/or extent of erythema (skin redness) and or the presence and/or extent of petechiae occurring at least during treatment, but preferably also before treatment. This feedback can then optimize the efficacy of the LIOB based treatment for skin rejuvenation by e.g. informing the user and/or disabling the device after recording an increase in erythema or petechiae with respect to respective baseline values that were preset by user or preprogrammed in a device or, more preferred, measured before or just at the start of the treatment. This feedback can reduce side-effects and social down time.

The threshold value for the increase in erythema can be programmable and therewith fine-tuned depending on the required coverage and severity of the side effect and subjective pain perception related to the LIOB treatment. The suitable threshold may vary between different subjects, and even for the same subject at different times.

Thus, the system of FIG. 3 may be used to analyze the level of skin redness.

The system of FIG. 3 may be modified by removing the image sensor 32 and lens 30 and instead providing an output window to enable visual inspection by a user of the system. The user can then visually inspect the skin redness at each laser flash.

However, the preferred option is to use the image sensor 32 for automatic analysis of the spectral content of the captured image using image processing of the image captured by the image sensor 32. In particular, changes in the spectral content, with an increase in red component, is detected when compared to an initial color at the beginning of the treatment. The image sensor may instead comprise a spectrophotometer.

In general, LIOB treatment leads to mild erythema immediately after treatment, and the severity increases for around 10 minutes. Erythema then fades and is no longer visible 30 minutes after treatment. It should not be allowed to pass a threshold of severity.

The image sensing may use high resolution photography, but low resolution photography using a low cost sensor is also sufficient to detect a red content in the image. Spectrophotometry may be performed, or image processing of a CCD image may be used.

Figure 6:
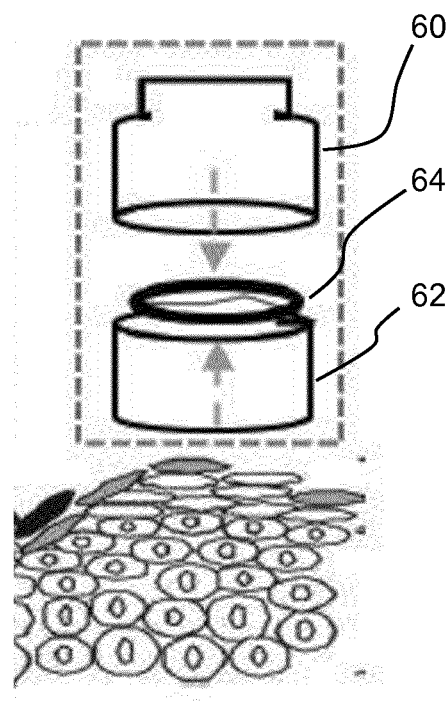
FIG. 6 is used to explain an optical feedback system.

FIG. 6 shows the image analysis system which comprises a high resolution camera 60 with built in image processing algorithms for quantitative cell analysis.

The camera 60 is integrated with an additional module consisting of a detachable mount 62. The camera unit consists of a LED illumination ring 64 and performs spatially resolved detection of backscattered light.

The increase in erythema is compared with a reference look-up table showing values corresponding to the treatment coverage area and specifying the limit of acceptable redness for the subject. Such data may be sub-divided to the different skin types that exist. An initial baseline measurement can be used as a calibration reference. The device may include a data link and processor enabling it to contact a remote database for retrieving such lookup data results if needed for a treatment or for storing such results during a treatment. The datalink may be based on internet technology or other remote networking technology as for example known in the art. The database may also be local as part of the device or via wired connection at the device location.

The skin status feedback may also be used in conjunction with the above feedback mechanisms based on sound, light or force.

To use the system for a treatment, an initial baseline skin color is recorded by the system, prior to any application of a mechanical redness provocation (tape stripping or other). This skin color is recoded from a skin area to be treated.

A comparison of an irritated skin or erythema (increase in redness) with the baseline skin may also be made before the treatment, so that the way a particular subject reacts to treatment can be recorded.

The LIOB treatment is then carried out.

The skin redness is recorded after the first treatment. A comparison is then made with respect to the desired erythema threshold, which in turn depends on the required treatment coverage area and acceptable subjective pain perception. The subject indicates their discomfort threshold by providing pain perception information during treatment and also by visual assessment of the irritated skin afterwards.

If the skin redness in the treated area is greater than the baseline skin color and has reached the threshold the treatment is stopped, otherwise the LIOB treatment is continued.

As mentioned above, Nd:YAG lasers with emission at 1064 nm may be used, but also or Er:YAG lasers with emission at 1645 nm may be used for laser induced optical breakdown (LIOB).

The skin treatment may comprise a hair removal shaving process. During use, the focusing system 23 is moved over the skin surface to be shaved. The focusing system forms an exit window for allowing the incident light beam to leave the device. The focusing system then forms an optical blade.

The skin treatment may comprise skin rejuvenation device for reducing wrinkles that may appear in human skin as a result of normal aging processes. During use, the focusing element is pressed onto or kept close to the skin to be treated. The exit window formed by the focusing system is held parallel to the skin and the incident light beam leaves the exit window and enters the skin in a direction substantially perpendicular to the skin surface.

In both examples, an immersion fluid may be provided between the focusing system and the skin surface. Preferably, an immersion fluid is used with a refractive index close to the refractive index of the skin contact lens of the focusing system 23 and the skin or hair where the LIOB is to occur. For this purpose, fluids with a refractive index of about 1.4 to about 1.5 are suitable. Also water, although having a somewhat lower refractive index of 1.33, may for some devices and applications be a suitable immersion fluid.

The system of FIG. 1 has one particular set of optical components between the laser and the focusing system. However, this arrangement is not intended to be limiting. The feedback system of the invention may be used in different system configurations with a smaller or greater number of components.

Summarizing, a pulsed laser skin treatment device is for laser induced optical breakdown of hair or skin tissue. The device has a light exit window to be placed against a surface to be treated such as skin during use. A feedback system is used for determining a state of contact between the light exit window and the surface. To this end the feedback system is capable of detecting a feedback signal representative for the state of contact. If the feedback signal or the state of contact is such that the risk of skin surface or device damage by the device operation is too high, the user or the device has a way to interrupt the treatment or to reduce light output to reduce or eliminate this risk.

The above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A device for treatment of tissue of a subject, the device comprising:
   a light source, the light source providing a pulsed light beam;
   a focusing system,
      wherein the focusing system is arranged to receive the pulsed light beam,
      wherein the focusing system is arranged to output a focused pulsed light beam,
      wherein the focused pulsed light beam has a focal spot that can be positioned in the tissue,
      wherein laser induced optical breakdown (LIOB) occurs when the focused pulsed light beam is focused on the focal spot;
   a light exit window, the light exit window having a contact surface,
      wherein the contact surface is arranged to contact an external surface of the subject during use of the device,
      wherein the light exit window allows the pulsed light beam to exit the device through the contact surface before it reaches the focal spot;
   wherein the device comprises a feedback system,
   wherein the feedback system detects a feedback signal dependent upon a state of contact between the contact surface and the tissue,
   wherein the feedback signal comprises sound generated by the LIOB of the focused pulsed light beam,
   wherein the feedback system comprises a device for detecting the sound generated by the LIOB,
   wherein the feedback system is arranged to determine the state of contact from one or more spectral characteristics of the sound generated by the LIOB
   wherein the spectral characteristics of the sound are indicative of material at the focal spot, and the feedback system determines the state of contact based on the indicated material at the focal spot.

2. The device as claimed in claim 1,
   wherein the feedback system comprises a user interface,
   wherein the user interface provides a user a representation of the feedback signal.

3. The device as claimed in claim 1, wherein the feedback system is arranged to change the power density of the focused pulsed light beam in dependence of the feedback signal.

4. The device as claimed in claim 3, wherein the changing of the power density comprises:
   comparing the feedback signal with a threshold signal,
      wherein the threshold signal is associated with a desired state of contact,
      wherein the desired state of contact is a state of contact that prevents substantial damage to the device or to the surface of the tissue, and
   reducing the power density when the comparison of the feedback signal with the threshold signal is indicative of a state of contact that does not correspond to the desired state of contact.

5. The device as claimed in claim 3, wherein the changing of the power density comprises changing the power of the focused pulsed light beam.

6. The device as claimed in claim 1,
   wherein the feedback signal comprises light dependent on the state of contact,
   wherein the feedback system comprises a device for detecting the light,
   wherein the feedback system is arranged to determine the state of contact from one or more characteristics of the light.

7. The device as claimed in claim 6, wherein the light is generated by the pulsed light beam.

8. The device as claimed in claim 6, wherein the light is originating from the contact surface.

9. The device as claimed in claim 6,
   wherein the device comprises an image sensor, wherein the feedback system is arranged to determine the state of contact from one or more characteristics of an image captured by the image sensor.

10. The device as claimed in claim 1,
wherein the feedback signal comprises a force or pressure dependent on the force or pressure with which the light exit window is pressed against the tissue during use of the device,
wherein the feedback system comprises a detector,
wherein the detector is arranged to detect the force or pressure,
wherein the feedback system is arranged to determine the state of contact based on the force or pressure.

11. A method of treatment of tissue of a subject, the method comprising:
providing a pulsed light beam;
focusing the pulsed light beam into a focused pulsed light beam,
wherein the focused pulsed light beam has a focal spot positioned in the tissue,
wherein laser induced optical breakdown (LIOB) occurs when the focused pulsed light beam is focused on the focal spot;
providing a light exit window, the light exit window having a contact surface in contact with an external surface of the subject,
wherein the light exit window allows the pulsed light beam to exit the device through the contact surface before it reaches the focal spot,
wherein the light exit window has a contact surface arranged to contact the tissue during use of the device;
detecting a feedback signal dependent on a state of contact between the contact surface and the tissue,
wherein the feedback signal comprises sound generated by the LIOB of the focused pulsed light beam,
wherein the feedback system comprises a device for detecting the sound generated by the LIOB,
wherein the feedback system is arranged to determine the state of contact from one or more spectral characteristics of the sound generated by the LIOB
wherein the spectral characteristics of the sound are indicative of the material at the focal spot, and the feedback system determines the state of contact based on the indicated material at the focal spot.

12. The method as claimed in claim 11, further comprising determining a state of contact based on the spectral characteristics of the sound within a range of 3 to 16 kHz.

13. The method as claimed in claim 11, further comprising changing the power density of the focused pulsed light beam in dependence of the feedback signal.

14. The method as claimed in claim 11, further comprising determining a state of contact based on the detected feedback signal.

15. The method as claimed in claim 11, further comprising changing the power density of the focused pulsed light beam in dependence of the determined state of contact.

16. The device as claimed in claim 1, wherein the feedback system is arranged to determine a state of contact from the spectral characteristics of the sound within a range of 3 to 16 kHz.

17. The device as claimed in claim 1,
wherein the feedback system comprises a user interface,
wherein the user interface provides a user an indication of the determined state of contact.

18. The device as claimed in claim 1, wherein the feedback system is arranged to change the power density of the focused pulsed light beam in dependence of the determined state of contact.

19. The device as claimed in claim 3, wherein the changing of the power density comprises changing the beam shape of the focused pulsed light beam.

20. The device as claimed in claim 6, wherein the light is generated by the focused pulsed light beam.

* * * * *